United States Patent [19]

Horn et al.

[11] 4,021,408

[45] May 3, 1977

[54] BIS-[4-m,m'-DI-TERT.-BUTYL-p-HYDROXYPHENYL)-BUTYL-(2)]DICARBOXYLIC ACID ESTERS

[75] Inventors: Peter Horn; Gernot Teege, both of Ludwigshafen; Werner Fliege, Otterstadt; Frank Weiss, Mannheim; Bernd Meissner, Heidelberg, all of Germany

[73] Assignee: BASF Aktiengesellschaft, Ludwigshafen, Germany

[22] Filed: Apr. 3, 1975

[21] Appl. No.: 564,617

[30] Foreign Application Priority Data

Apr. 25, 1974 Germany ............................ 2420006

[52] U.S. Cl. ..................... 260/45.85 T; 260/475 P; 260/485 G

[51] Int. Cl.² ..................... C08K 5/13; C07C 39/12

[58] Field of Search ................ 260/45.85 T, 475 P, 260/485 G

[56] References Cited

UNITED STATES PATENTS

| | | | |
|---|---|---|---|
| 3,116,305 | 12/1963 | Morris et al. | 260/45.85 T |
| 3,294,836 | 12/1966 | Peterson et al. | 260/475 P |
| 3,422,059 | 1/1969 | Taylor et al. | 260/475 P |
| 3,795,700 | 3/1974 | Song et al. | 260/45.85 T |
| 3,810,929 | 5/1974 | Song | 260/45.85 T |

*Primary Examiner*—V. P. Hoke
*Attorney, Agent, or Firm*—Johnston, Keil, Thompson & Shurtleff

[57] ABSTRACT

New bis-[4-(m,m'-di-tert.-butyl-p-hydroxyphenyl)-butyl-(2)] dicarboxylic acid esters which are starting materials for the manufacture of dyes, pesticides and additives for plastics, especially stabilizers for polyolefins and polyamides, and are themselves stabilizers, aging retardants or antioxidants for organic products.

10 Claims, No Drawings

BIS-[4-(m,m'-DI-TERT.-BUTYL-p-HYDROXY-PHENYL)-BUTYL-(2)]DICARBOXYLIC ACID ESTERS

The present invention relates to new bis-[4-(m,m'-di-tert.-butyl-p-hydroxyphenyl)-butyl-(2)] dicarboxylic acid esters.

We have found new bis-[4-(m,m'-di-tert.-butyl-p-hydroxyphenyl)-butyl-(2)] dicarboxylic acid esters of the formula

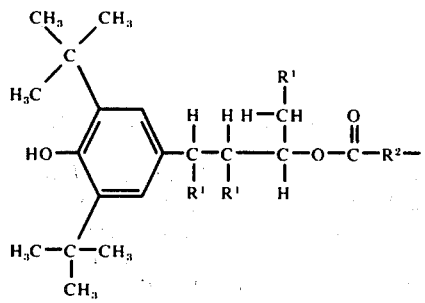

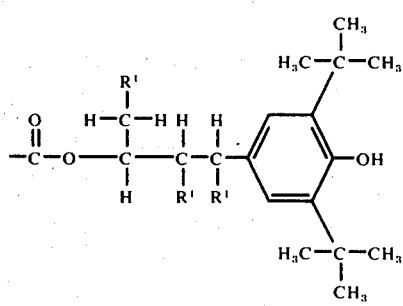

wherein the $R^1$'s are identical or different and each is hydrogen or an aliphatic radical and $R^2$ is an aliphatic, cycloaliphatic, araliphatic or aromatic radical.

Preferred products are the new bis-[4-(m,m'-di-tert.-butyl-p-hydroxyphenyl)-butyl-(2)] dicarboxylic acid esters of the formula

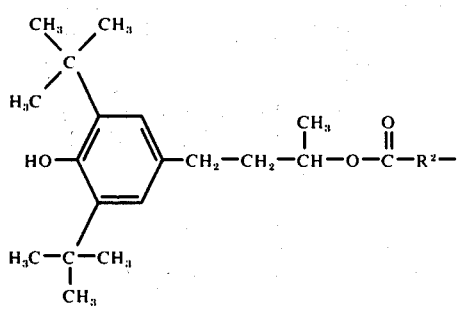

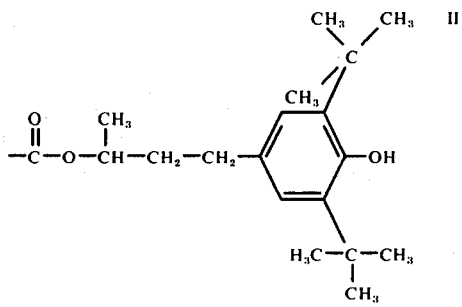

wherein $R^2$ is an aliphatic, cycloaliphatic, araliphatic or aromatic radical.

The new compounds may be manufactured by conventional methods of synthesizing dicarboxylic acid esters. Advantageously, the esters of the formula I are manufactured by reacting a 4-(m,m'-di-tert.-butyl-p-hydroxyphenyl)-butan-2-ol of the formula

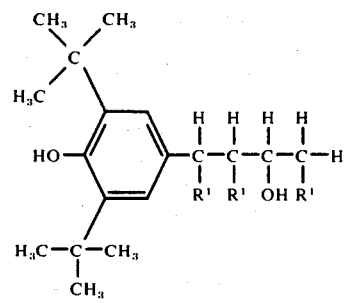

with a dicarboxylic acid, or a derivative of a dicarboxylic acid, of the formula

wherein $R^1$ and $R^2$ have the above meanings. The starting materials III may be manufactured by conventional methods.

If 4-(m,m'-di-tert.-butyl-p-hydroxyphenyl)-butan-2-ol and terephthalic acid dichloride are used, the reaction may be represented by the following equation:

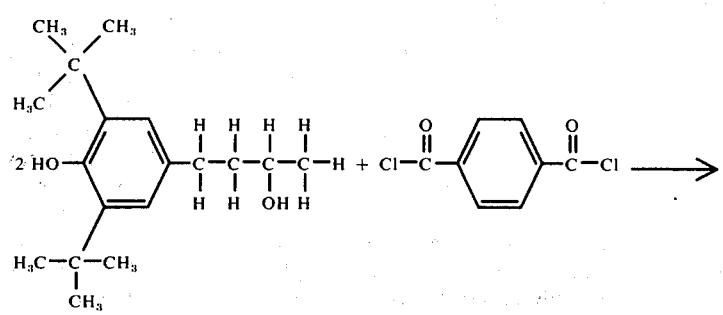

-continued

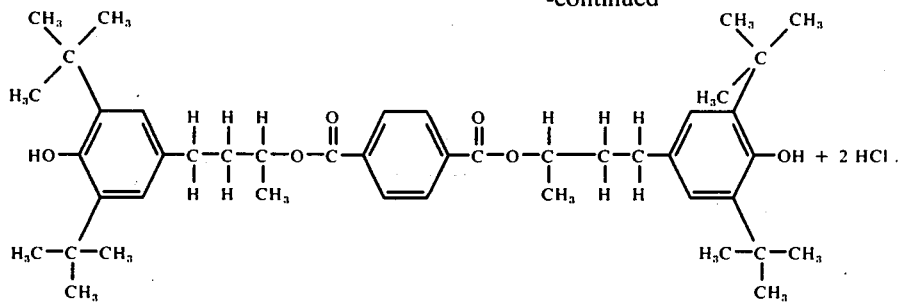

Preferred starting materials III and IV and, accordingly, preferred products I are those wherein the $R^1$'s are identical or different and each is alkyl of 1 to 4 carbon atoms or, in particular, hydrogen, and $R^2$ is alkylene of 1 to 20 carbon atoms, especially of 1 to 6 carbon atoms, cyclohexylene, aralkylene of 8 to 12 carbon atoms, naphthylene or phenylene. The above radicals may in addition be substituted by groups which are inert under the reaction conditions, e.g., alkyl or alkoxy each of 1 to 4 carbon atoms, or nitro. 4-(m,m'-di-tert.-butyl-p-hydroxyphenyl)-butan-2-ol is a particularly advantageous starting material III. Further examples of starting materials III are 4-methyl-, 3-ethyl-, 1-ethyl-, 1,4-dimethyl- and 1,3,4-trimethyl-4-(m,m'-di-tert.-butyl-p-hydroxyphenyl)-butan-2-ol. The starting materials IV are dicarboxylic acids or derivatives of such carboxylic acids, e.g. the halides, preferably the chlorides, and simple or mixed anhydrides. Examples of suitable starting materials are adipic acid, succinic acid, malonic acid, glutaric acid, pimelic acid, suberic acid, azelaic acid, sebacic acid, nonanedicarboxylic acid, decanedicarboxylic acid, undecanedicarboxylic acid, dodecanedicarboxylic acid, cyclohexane-1,2-dicarboxylic acid, cyclohexane-1,3-dicarboxylic acid, cyclohexane-1,4-dicarboxylic acid, 1,2-cyclopentanedicarboxylic acid, 1,2-, 1,3- and 1,4-benzenediacetic acid, o-, m- and p-carboxyphenylacetic acid, o-carboxy-hydrocinnamic acid, o-carboxyphenylbutyric acid, o-, m- and p-phenylene-dipropionic acid, terephthalic acid, phthalic acid, isophthalic acid, o-carboxymethylphenylpropionic acid, nitroterephthalic acid, methylterephthalic acid, 2,5-dimethoxyterephthalic acid, 4-methoxyisophthalic acid, 4-methylisophthalic acid and analogous acid halides and acid anhydrides.

The starting material III may be reacted with a stoichiometric amount or an excess of the starting material IV; preferably, from 1.1 to 1.3 moles of starting material IV are employed per mole of starting material III. The reaction is as a rule carried out at from 10° to 170° C, preferably at from 20° to 90° C, under atmospheric or superatmospheric pressure, continuously or batchwise. Preferably, solvents are used, such as ketones, e.g. acetone, aliphatic hydrocarbons, e.g. gasoline or hexane, ethers, e.g. dipropyl ether, tetrahydrofuran or dioxane, aromatic hydrocarbons, e.g. benzene, toluene or xylenes, or chlorohydrocarbons, e.g. chloroform or methylene chloride.

Where dicarboxylic acids are used as starting materials IV, acids such as phosphoric acid, aromatic sulfonic acids, e.g. p-toluenesulfonic acid, or, preferably, hydrogen chloride or sulfuric acid are added as catalysts; advantageous amounts to use are, in particular, from 0.5 to 15, especially from 3 to 10, % by weight of acid, based on dicarboxylic acid IV. Where appropriate, compounds which bind the water formed, e.g. anhydrous salts such as copper sulfate and iron sulfate, may also be present. Esterification catalysts such as acid chlorides, for example thionyl chloride, chlorosulfonic acid or ansolvo-acids such as boron trifluoride may also be present, or special esterification operations, e.g. esterification accompanied by azeotropic distillation with, e.g., benzene or toluene, may be used.

It is also possible to trans-esterify esters of the dicarboxylic acids IV, preferably esters with lower alkanols such as methanol or ethanol, with the starting material III. Expediently, an excess, e.g. a 3-fold to 10-fold excess, of the starting material III, based on the stoichiometric amount of ester, is used, and the alkanol eliminated during the reaction is distilled off simultaneously. Preferably, however, halides of the dicarboxylic acids IV, in particular the chlorides, are used as starting materials; they may, if appropriate, be formed in situ in the reaction mixture by using the dicarboxylic acids IV and acid chlorides such as phosphorus trichloride, phosphorus oxychloride, phosphorus pentachloride and thionyl chloride. Reaction of the starting materials III with the acid anhydride or, preferably, the acid halide in the presence of pyridine or a tertiary amine such as triethylamine, using from 200 to 1,000 mole% of amine, based on acid derivative, is preferred; in this variant, the halide may, if appropriate, be formed in situ in the reaction mixture from the acid and, e.g., phosgene. The amounts of anhydride or halide used and the reaction conditions correspond to the conditions given above for the reaction using dicarboxylic acids. With regard to details of the esterification reaction, reference may be made to Houben-Weyl, Methoden der Organischen Chemie, volume 8, pages 516 to 549.

The reaction may be carried out as follows: a mixture of the starting materials III and IV or of derivatives of the starting materials IV, if appropriate together with a solvent, esterification catalyst, acid and/or pyridine, is kept at the above temperature for from 1 to 12 hours whilst stirring. The ester I is then isolated by conventional methods, for example by mixing with ice, acidifying, extracting the mixture with, e.g., benzene and fractional distillation of the organic phase formed, or by filtration and fractional distillation of the filtrate.

The bis-[4-(m,m'-di-tert.-butyl-p-hydroxyphenyl)-butyl-(2)] dicarboxylic acid esters I which may be manufactured as described above, in particular the dicarboxylic acid esters of 4-(m,m'-di-tert.-butyl-p-hydroxyphenyl)-butan-2-ol, are valuable starting materials for the manufacture of dyes, pesticides and additives for plastics, especially stabilizers for polyolefins and polyamides. As melts, they are specific solvents for alkylphenols, e.g. 2,6-diethylphenol, 2,6-dimethylphenol and 2,4-dimethylphenol, and for disubstituted ureas, e.g. diphenylurea.

The compounds I are also themselves stabilizers, aging retardants or antioxidants for organic products which are deformed, embrittled, discolored or otherwise decomposed by the action of heat, light, oxygen or ozone. Examples of such organic products are lubricating oils, fuel oils, oils of mineral, vegetable or animal origin, waxes, soaps, fats, gasolines, natural and synthetic rubber, natural resins and plastics such as polyolefins, e.g. polyethylene and polypropylene, and polyamides.

Advantageous compounds I to use for the above purpose are bis-[4-(m,m'-di-tert.-butyl-p-hydroxyphenyl)-butyl-(2)] dicarboxylic acid esters of the formula

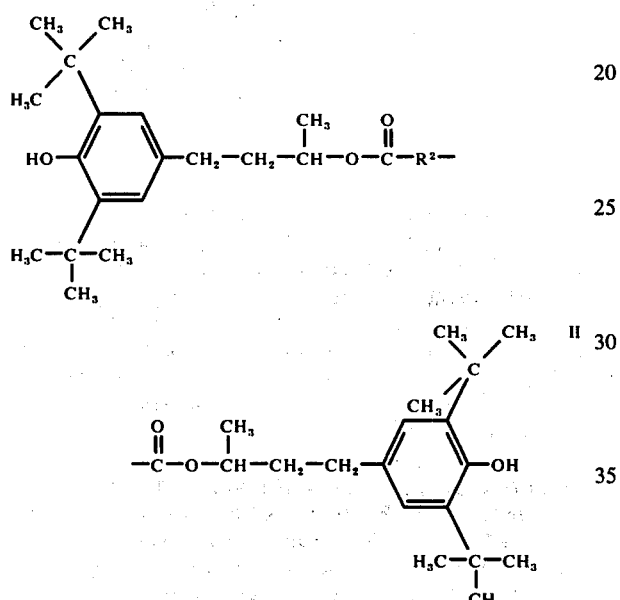

wherein $R^2$ is an aliphatic, cycloaliphatic, araliphatic or aromatic radical. Particularly preferred compounds I are those wherein $R^2$ is phenylene, or alkylene of 4 carbon atoms. Particularly advantageous products I are the following:

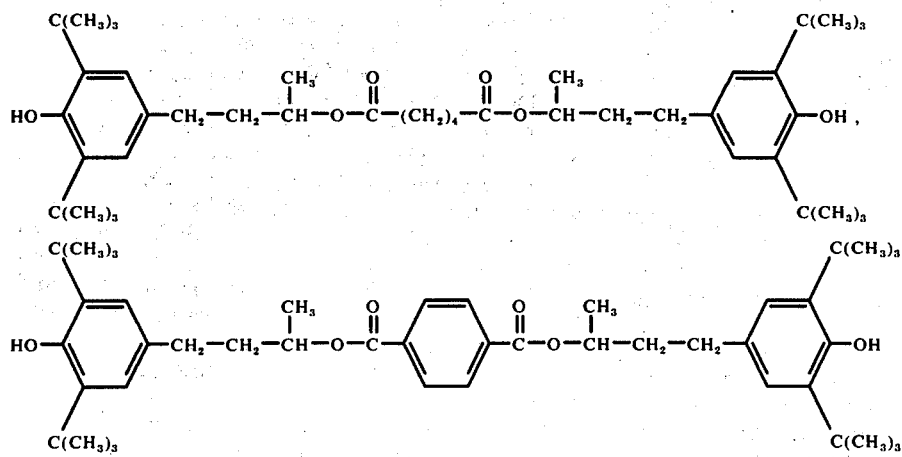

By way of example, the products I may be used as stabilizers for polyolefins, in amounts of from 0.05 to 3, preferably from 0.05 to 0.3, % by weight, based on the polyolefin (see also Examples 3 and 4). We have found that stabilized polyolefin molding materials are obtained from 1. a polyolefin,
2. from 0.05 to 3, preferably from 0.05 to 0.3, % by weight (based on the polyolefin) of a stabilizer, and, optionally,
3. conventional auxiliaries and adjuvants in conventional amounts, if the molding materials of the invention contain, as the stabilizer, a bis-[4-(m,m'-di-tert.-butyl-p-hydroxyphenyl)-butyl-(2)] dicarboxylic acid ester of the formula

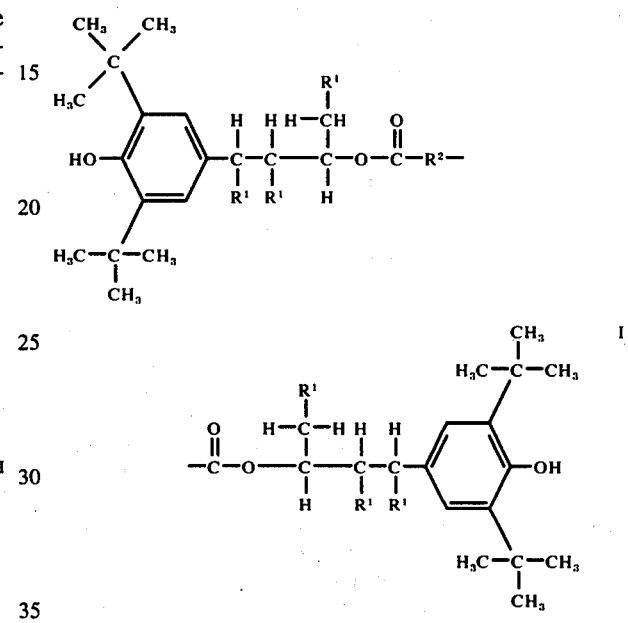

wherein the $R^1$'s are identical or different and each is hydrogen or an aliphatic radical and $R^2$ is an aliphatic, cycloaliphatic, araliphatic or aromatic radical.

A series of variants of molding materials of this type are known. In them, the stabilizer serves to protect polyolefins against harmful external factors, particularly to protect the polyolefins against the effects of heat, light and/or atmospheric oxygen. The stabilizers must conform to stringent standards. Thus, their action should in general be as broad as possible, i.e. they should act as stabilizers against as many detrimental factors as possible. In addition, they should in general have as long a life as possible and be very compatible with the polyolefin concerned (e.g., they should not exude from the polyolefin). In addition, the stabilizers, for their part, should have as little adverse effect as possible on such desirable properties as the polyolefins already possess, one of which is frequently their physiological harmlessness. Finally, the stabilizers should be inexpensive, i.e. readily obtainable, easy to handle and effective even in very small amounts. Compared to the products I, the conventional stabilizers in one way or another do not conform to the above standard to the desired degree, and in particular frequently do not do so because their desirable properties are accompanied by an undesirable property. The molding materials may contain individual products I or mixtures of two or more such products. The molding materials may be based on polyolefins which are conventionally used for the purpose in the plastics industry, i.e. in the main homopolymers and copolymers of α-olefins of 2 to 6 carbon atoms. We have found that the stabilizers of the invention are very suitable for stabilizing homopolymers and copolymers of ethylene and copolymers of propylene, but above all for stabilizing polyethylene manufactured by the high pressure process, and propylene homopolymers ("polypropylene"). The molding materials according to the invention may — if desired — additionally to the above stabilizers contain conventional auxiliaries and adjuvants in conventional amounts, e.g. other stabilizers, lubricants, agents to improve transparency, colorants, flameproofing agents and pulverulent or fibrous fillers and reinforcing agents. However, within the scope of the present invention such constituents are not a characterizing feature. The polyolefin molding material of the invention can easily be manufactured from the constituents, in the same way as additives are conventionally incorporated very homogeneously into the polyolefins concerned, e.g. by milling or extrusion. The conversion of the molding materials to moldings may be carried out easily with the equipment and processes conventionally used for the polyolefins concerned.

The products I are also used with advantage for stabilizing polyamides against oxidative factors and thermal degradation. It is known to stabilize polyamides against the effect of heat and air by adding, e.g., phosphites, complex copper/alkali metal halide compounds, phenolic compounds or aromatic amines. Polyamides containing any of these stabilizers still prove to have inadequate performance for many purposes. Thus, for example, the combination of copper salt/halide loses its stabilizing action entirely in the presence of certain colored pigments, e.g. cadmium pigments or zinc sulfide. Other stabilizers, e.g. the p-phenylenediamine derivatives, cause discoloration and are not physiologically harmless. Yet other stabilizers are either excessively volatile when incorporated into a polyamide melt, e.g., 2,6-di-tert.-butyl-4-methyl-phenol, discolor, e.g., 2,2'-methylene-bis-(4-methyl-6-tert.-butyl-phenol), or are insufficiently powerful stabilizers, e.g. 1,3,4-trimethyl-2,4,6-tri-(3',5'-di-tert.-butyl-4'-hydroxybenzyl)-benzene or pentaerythritol β-(3,5-di-tert.-butyl-4-hydroxyphenyl)-propionate. We have found that, surprisingly, the stabilization and non-discoloration of polyamides, particularly in the presence of pigments, can be improved, and polyamides can with advantage be stabilized against oxidative attack and thermal degradation, by using, as the stabilizers, bis-[4-(m,m'-di-tert.-butyl-p-hydroxyphenyl)-butyl-(2)] dicarboxylic acid esters of the formula

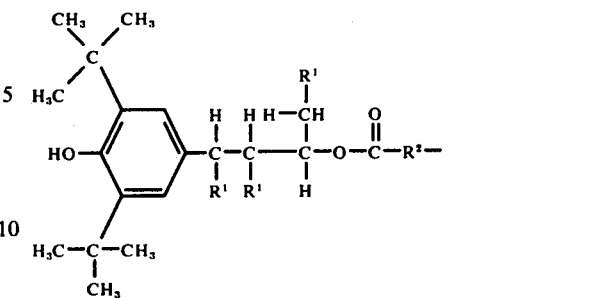

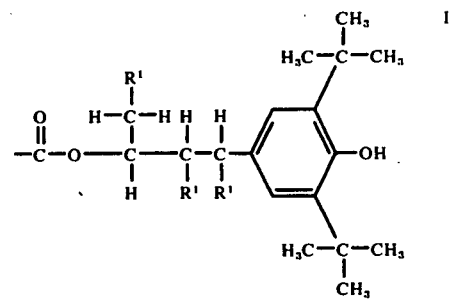

wherein the $R^1$'s are identical or different and each is hydrogen or an aliphatic radical and $R^2$ is an aliphatic, cycloaliphatic, araliphatic or aromatic radical.

For the stabilization of polyamides, from 0.01 to 2, preferably from 0.1 to 1, % by weight of product I, based on the polymer, is used. The stabilizer can be added to the monomeric starting materials for the polyamide before polymerization but can also be added during polymerization or by working into the finished polyamide. The conventional processes, such as are described, e.g., in Kunststoff-Handbuch, volume VI, Polyamides, Munich, 1966, may be used for these purposes. The compounds stabilize all polyamides and copolyamides, and polyamide mixtures, formed from conventional polyamide-forming compounds such as lactams, diamines and dicarboxylic acids, and aminocarboxylic acids. Examples of polyamide-forming lactams are pyrrolidone, caprolactam, capryllactam, enantholactam, aminoundecanelactam and lauryllactam; these may be polymerized, individually or as mixtures, by cationic mechanisms. Examples of polycondensates of diamines and dicarboxylic acids are those which may be manufactured from aliphatic dicarboxylic acids of 4 to 18 carbon atoms and diamines of 4 to 18 carbon atoms, in particular nylon 6, 6 and nylon 6, 10. The stabilizers of the invention give polyamides which are free from discoloration and which have much more stable properties, even on severe exposure to heat and oxidative factors, that do polyamides containing conventional phenolic stabilizers. The stabilizers of the invention can be used both for polyamides intended for the manufacture of moldings and for polyamides intended for the manufacture of fibers and filaments. They are particularly suitable for use with colored polyamides, since they do not interfere with the color characteristics. This is true particularly if pigments are used. In addition, the polyamides may, without detriment, contain conventional fillers, e.g. glass fibers, other polymers, lubricants, crystallization accelerators and other conventional additives, as well as additional stabilizers.

The examples which follow illustrate the method of stabilization using the stabilizers described above, and the mode of action of the latter. The notched impact strength of standard test bars according to DIN 53,453 is measured as a characteristic mechanical property, for the purpose of testing the aging properties (or heat resistance). The standard bars, of size 4 × 6 × 50 mm, are provided with a central hole of 3 mm diameter and are stored for 30 days in air at 140° C. Per material sample, 10 bars are respectively withdrawn from the test after 3, 10, 20 and 30 days and their notched impact strength is determined as described in Kunststoffe 57 (1967), pages 825 to 828.

In the Examples which follow, parts are by weight and bear the same relation to parts by volume as the kilogram to the liter.

EXAMPLE 1

0.51 part of terephthalic acid dichloride in 1 part by volume of toluene is added slowly to 1.39 parts of 4-(m,m'-di-tert.-butyl-p-hydroxyphenyl)-butan-2-ol, 0.405 part by volume of pyridine and 2 parts by volume of toluene at 50° C. The reaction mixture is kept at this temperature for 1 hour and then cooled, after which the pyridine hydrochloride which has precipitated is separated off and the solvent is removed. This viscous, oily residue is dissolved in warm methanol; on slow cooling, 1.63 parts of the terephthalic acid diester of 4-(3,5-di-tert.-butyl-4-hydroxyphenyl)-butan-2-ol (95% of theory) are obtained as a diastereomeric mixture melting at from 90° to 140° C (racemate and meso-form).

On digesting the oily residue with cyclohexane, a diastereomer melting at from 154° to 146° C is obtained.

EXAMPLE 2

0.46 part of adipic acid dichloride is added slowly to 1.39 parts of 4-(3,5-di-tert.-butyl-4-hydroxyphenyl)-butan-2-ol, 0.405 part by volume of pyridine and 2 parts by volume of toluene at 40° C. The mixture is additionally heated to 60° C for one hour and is then allowed to cool, and the pyridine hydrochloride which has precipitated is separated off. After removing the solvent, 1.66 parts of the adipic acid diester of 4-(3,5-di-tert.-butyl-4-hydroxyphenyl)-butan-2-ol, boilind at 230° C/$10^{-4}$ mm Hg, are obtained. The yield is practically quantitative.

EXAMPLE 3

Polypropylene is mixed with 0.2% by weight of the bis-[4-(m,m'-di-tert.-butyl-p-phydroxyphenyl)-but-2-yl] terephthalate obtained in Example 1, and fused. The stabilized polypropylene is then milled to form 1 mm thick sheets from which plaques of size 15 × 40 × 1 mm are cut. These are suspended in a heating chamber through which air at 140° C is passed constantly. Plaques, of the same size, of unstabilized polypropylene are tested at the same time for comparison. The plaques are contantly agitated by means of a mechanical device. This aging test serves to examine the decomposition of polypropylene under accelerated conditions. In contrast to the unstabilized polypropylene plaques, which show signs of decomposition after only a few hours, no oxidative decomposition or discoloration is detectable in the stabilized polypropylene plaques after 1,050 hours.

EXAMPLE 4

0.05% by weight of the terephthalic acid diester obtained in Example 1 is worked into high pressure polyethylene by milling at 140° C. The oxidative stability of 1 mm thick plaques produced from the milled hide is determined by storing the plaques in an oxygen atmosphere at 180° C and measuring the decrease in volume. The time up to the first change in volume (the induction period $t_I$) of the oxygen-filled gas space, and the times to reach a volume decrease of 2, 5, 10, 15 and 20 ml of $O_2$ are measured.

Unstabilized high pressure polyethylene is used for comparison.

TABLE 1

| | $t_I$ (minutes) | 2 | 5 | 10 | 15 | 20 | ml $O_2$ |
|---|---|---|---|---|---|---|---|
| Unstabilized polyethylene | 11 | 14 | 21 | 30 | 39 | 49 | minutes |
| Stabilized polyethylene | 58 | 63 | 70 | 79 | 88 | 97 | minutes |

EXAMPLE 5

Starting material:
A polypropylene molding material containing
1. a polypropylene of intrinsic viscosity ($\eta$) (measured in decalin at 130° C) of 2.5 dl/g, and containing 15 percent by weight of material soluble in boiling n-heptane, and
2. 0.2 percent by weight, based on polypropylene, of the stabilizer (adipic acid diester of 4-(m,m'-di-tert.-butyl-p-hydroxyphenyl)-2-hydroxybutane).

Apparatus:
A conventional apparatus for the manufacture of blow film.

Method:
A blown film is produced by using the molding material to extrude a primary tube of 0.07 mm wall thickness through an annular die (material temperature during extrusion: 210° C), inflating the tube to 1.5 times its original internal diameter and at the same time cooling it to 50° C, at a take-off speed of 12 m/sec.

A blown film which exhibits good properties, and in particular very good stabilization to heat, light and atmospheric oxygen, is obtained.

EXAMPLE 6

Starting material:
A polypropylene molding material containing
1. a polypropylene as in Example 5 except that it contains 3 percent by weight of material soluble in boiling n-heptane and
2. 0.2 percent by weight -based on the polypropylene - of the terephthalic acid diester of 4-(m,m'-di-tert.-butyl-p-hydroxyphenyl)-2-hydroxybutane.

Apparatus:
A conventional apparatus for the manufacture of injection moldings (a screw injection molding machine with 400 g maximum shot weight, 300 megapond clamping force and 1,600 kp/cm² maximum theoretical injection pressure in front of the screw).

Method:

Rectangular open boxes (width 60 mm, length 120 mm, height 40 mm) are produced on the screw injection molding machine.

Conditions:
Melt temperature: 250° C.
Cycle time: 60 seconds.
Temperature of the cooling medium (water): 30° C.
The mold release temperature is such that no deformation of the molding occurs.

Moldings which exhibit better stabilization than is achievable with the same polypropylene and conventional stabilizers under otherwise identical conditions are obtained.

EXAMPLE 7

Starting material:
A polypropylene molding material containing
1. a polypropylene as in Example 5 and
2. 0.2 percent by weight, based on polypropylene, of the adipic acid diester of 4-(m,m'-di-tert.-butyl-p-hydroxyphenyl)-2-hydroxybutane.

Processing:
The method of Example 6 is followed.
Moldings which exhibit good properties, and in particular very good stabilization, are obtained.

EXAMPLE 8

Starting material:
A polypropylene molding material containing
1. a polypropylene as in Example 5 except that it contains 3 percent by weight of material soluble in boiling n-heptane and
2. 0.2 percent by weight — based on polypropylene — of the terephthalic acid diester of 4-(m,m'-di-tert.-butyl-p-hydroxyphenyl)-2-hydroxybutane.

Processing:
The method of Example 5 is used.
Films which exhibit better stabilization than is achievable with the same polypropylene and conventional stabilizers under otherwise identical conditions are obtained.

EXAMPLE 9

200 parts of polycaprolactam granules of K value 72 (determined on a 1 percent strength by weight solution in concentrated sulfuric acid) are mixed mechanically with 1 part of the terephthalic acid diester obtained in Example 1 and the mixture is fused, and extruded, using a twin-screw kneader heated to 270° C, the residence time of the mixture in the kneader being 5 minutes. The extruded mixture is granulated and dried and standard bars according to DIN 53,453 are molded from the mixture on an injection molding machine. The molecular weight corresponds, within the limits of error, to the initial polycaprolactam. The color of the standard bars is assessed visually, and the notched impact strength is measured. The results are shown in Table 2.

TABLE 2

| Color of the molding | Notched impact strength (cmkp/cm²) after | | | | | |
|---|---|---|---|---|---|---|
| | 0 | 2 | 5 | 10 | 20 | 30 days |
| Unstabilized polyamide — Colorless | 67 | 7.7 | 2.6 | 2.2 | 1.5 | 1.5 |
| Stabilized polyamide — Like the initial polyamide | 78.3 | 72.5 | 65.8 | 53.2 | 6.2 | 2.5 |

We claim:
1. Bis-[4-(m,m'-di-tert.-butyl-p-hydroxyphenyl)-butyl-(2)] dicarboxylic acid esters of the formula

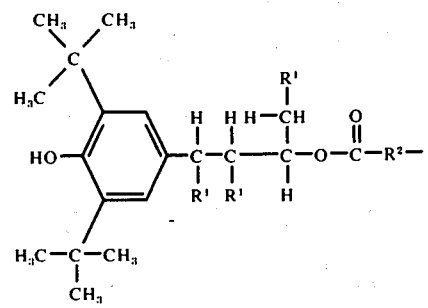

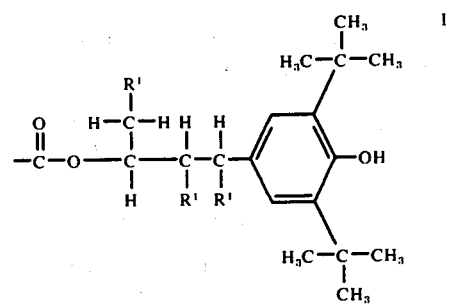

wherein the $R^1$'s are identical or different and each is hydrogen or an aliphatic radical and $R^2$ is an aliphatic, cycloaliphatic, araliphatic or aromatic radical.

2. Bis-[4-(m,m'-di-tert.-butyl-p-hydroxyphenyl)-butyl-(2)] dicarboxylic acid esters of the formula

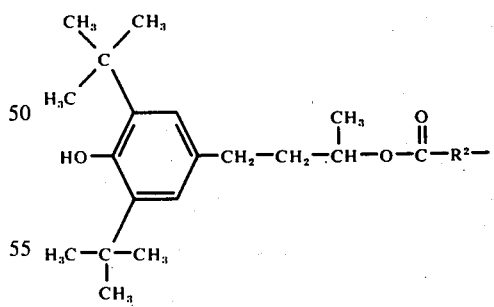

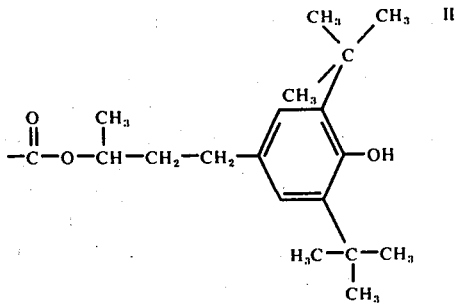

wherein R² is an aliphatic, cycloaliphatic, araliphatic or aromatic radical.

3. Bis-[4-(m,m'-di-tert.-butyl-p-hydroxyphenyl)-butyl-(2)] adipate.

4. Bis-[4-(m,m'-di-tert.-butyl-p-hydroxyphenyl)-butyl-(2)] terephthalate.

5. A process for stabilizing plastics, wherein the stabilizers used are bis-[4-(m,m'-di-tert.-butyl-p-hydroxyphenyl)-butyl-(2)] dicarboxylic acid esters of the formula

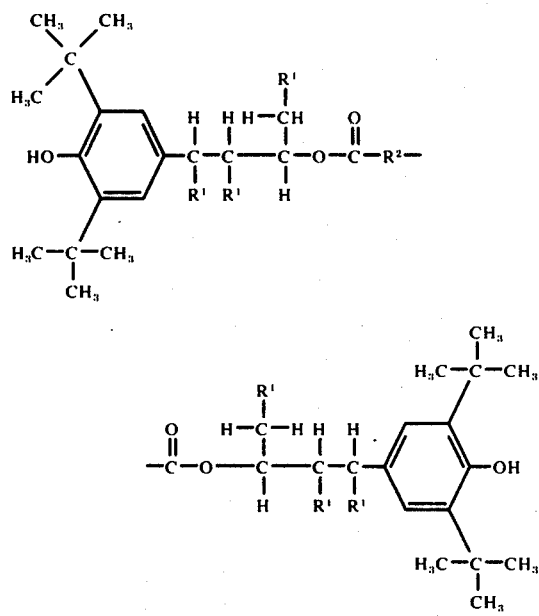

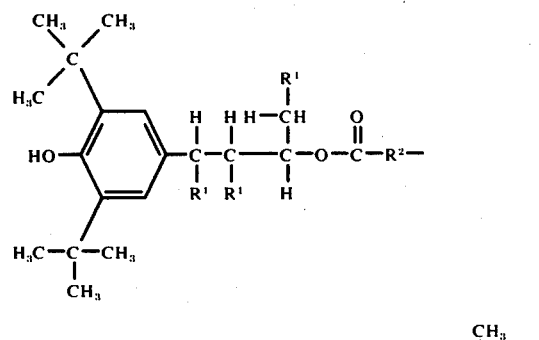

wherein the R¹'s are identical or different and each is hydrogen or an aliphatic radical and R² is an aliphatic, cycloaliphatic, araliphatic or aromatic radical.

6. A process for stabilizing polyamides against oxidative deterioration and thermal degradation, wherein the stabilizers used are bis-[4-(m,m'-di-tert.-butyl-p-hydroxyphenyl)-butyl-(2)] dicarboxylic acid esters of the formula

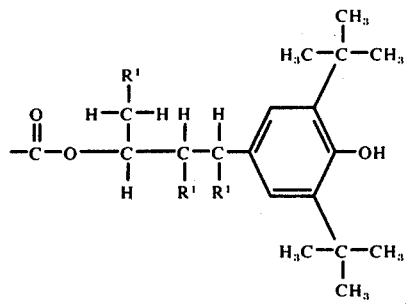

wherein the R¹'s are identical or different and ech is hydrogen or an aliphatic radical and R² is an aliphatic, cycloaliphatic, araliphatic or aromatic radical.

7. Bis-[4-m,m'-di-tert.-butyl-p-hydroxyphenyl)-butyl-(2)] dicarboxylic acid esters of the formula

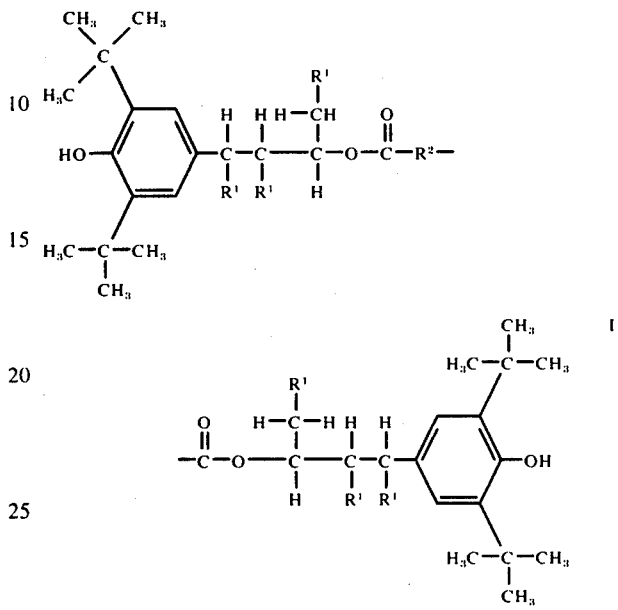

wherein the R¹'s are identical or different and each is alkyl of 1 to 4 carbon atoms or hydrogen and R² is alkylene of 1 to 20 carbon atoms, cyclohexylene, aralkylene of 8 to 12 carbon atoms, naphthylene or phenylene and the above radicals may in addition be substituted by alkyl or alkoxy each of 1 to 4 carbon atoms or by nitro.

8. A process as set forth in claim 6 wherein the R¹'s are identical or different and each of alkyl of 1 to 4 carbon atoms or hydrogen an R² is alkylene of 1 to 20 carbon atoms, cyclohexylene, aralkylene of 8 to 12 carbon atoms, naphthylene or phenylene and the above radicals may in addition be substituted by alkyl or alkoxy each of 1 to 4 carbon atomsor by atoms or 9. A polyolefin composition comprising a polyolefin and a thermooxidative stabilizing amount of a compound having the formula

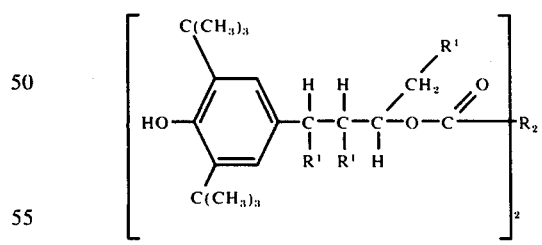

wherein the R¹'s are identical or different and each is hydrogen or an aliphatic radical and R² is an aliphatic, cycloaliphatic, araliphatic or aromatic radical.

10. A stabilized polyolefin molding material as set forth in claim 9 wherein the R¹'s are identical or different and ech is alkyl of 1 to 4 carbon atoms or hydrogen and R² is alkylene of 1 to 20 carbon atoms, cyclohexylene, aralkylene of 8 to 12 carbon atoms, naphthylene or phenylene and the above radicals may in addition be substituted by alkyl or alkoxy each of 1 to 4 carbon atoms or by nitro.

* * * * *